United States Patent
Kipke et al.

(10) Patent No.: US 6,829,498 B2
(45) Date of Patent: Dec. 7, 2004

(54) DEVICE FOR CREATING A NEURAL INTERFACE AND METHOD FOR MAKING SAME

(75) Inventors: Daryl Kipke, Dexter, MI (US); Justin Williams, Tempe, AZ (US); Patrick Rousche, Tempe, AZ (US); David S. Pellinen, Tempe, AZ (US); David Pivin, Phoenix, AZ (US)

(73) Assignee: Arizona Board of Regents, Phoenix, AZ (US)

( * ) Notice: Subject to any disclaimer, the term of this patent is extended or adjusted under 35 U.S.C. 154(b) by 143 days.

(21) Appl. No.: 09/979,320
(22) PCT Filed: Mar. 29, 2001
(86) PCT No.: PCT/US01/10032

§ 371 (c)(1),
(2), (4) Date: Nov. 16, 2001

(87) PCT Pub. No.: WO01/72201

PCT Pub. Date: Oct. 4, 2001

(65) Prior Publication Data

US 2003/0100823 A1 May 29, 2003

Related U.S. Application Data

(60) Provisional application No. 60/193,031, filed on Mar. 29, 2000.

(51) Int. Cl.$^7$ .............................. A61B 5/04; A61N 1/05
(52) U.S. Cl. ......................... 600/378; 607/116; 29/825
(58) Field of Search ................................. 600/373, 378, 600/379; 607/116, 117, 118; 29/825

(56) References Cited

U.S. PATENT DOCUMENTS

| | | | |
|---|---|---|---|
| 5,178,161 A | | 1/1993 | Kovacs |
| 5,178,957 A | * | 1/1993 | Kolpe et al. ................ 428/458 |
| 5,215,088 A | | 6/1993 | Normann et al. |
| 5,376,128 A | | 12/1994 | Bozeman, Jr. et al. |
| 5,524,338 A | | 6/1996 | Martyniuk et al. |
| 5,897,583 A | * | 4/1999 | Meyer et al. ................ 607/116 |
| 6,330,466 B1 | * | 12/2001 | Hofmann et al. ........... 600/378 |
| 6,368,147 B1 | * | 4/2002 | Swanson ..................... 439/496 |
| 6,402,689 B1 | * | 6/2002 | Scarantino et al. ......... 600/300 |

OTHER PUBLICATIONS

Stieglitz et al, "Flexible, Polyimide–Based Neural Interfaces" Seventh International Conference on Microelectronics for Neural, fuzzy and Bio–Inspired Systems, Apr. 7–9, 1999.*

* cited by examiner

*Primary Examiner*—Lee S. Cohen
(74) *Attorney, Agent, or Firm*—Snell & Wilmer L.L.P.

(57) ABSTRACT

An implant device for creating a neural interface with the central nervous system having a polyimide-based electrode array is presented along with a method for making the device. The device may be configured as a three dimensional structure and is capable of sensing multi-unit neural activity from the cerebral cortex. Mechanical, electrical and biological characteristics of the device support its use as a reliable, long term implant.

35 Claims, 6 Drawing Sheets

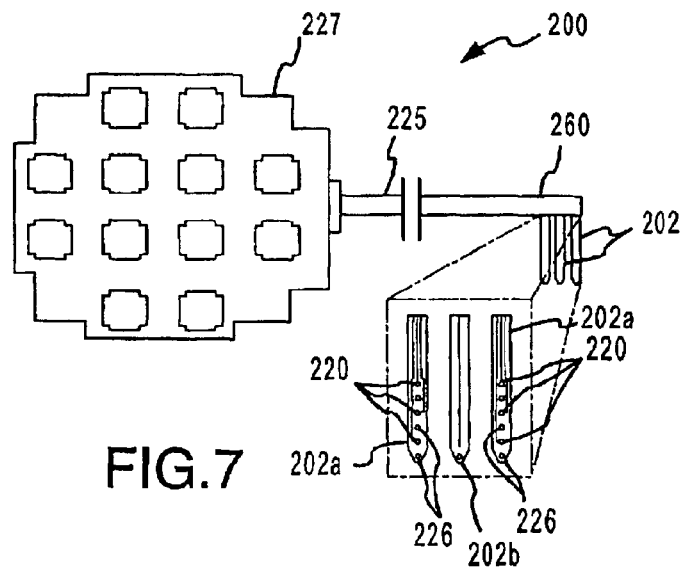
FIG.7
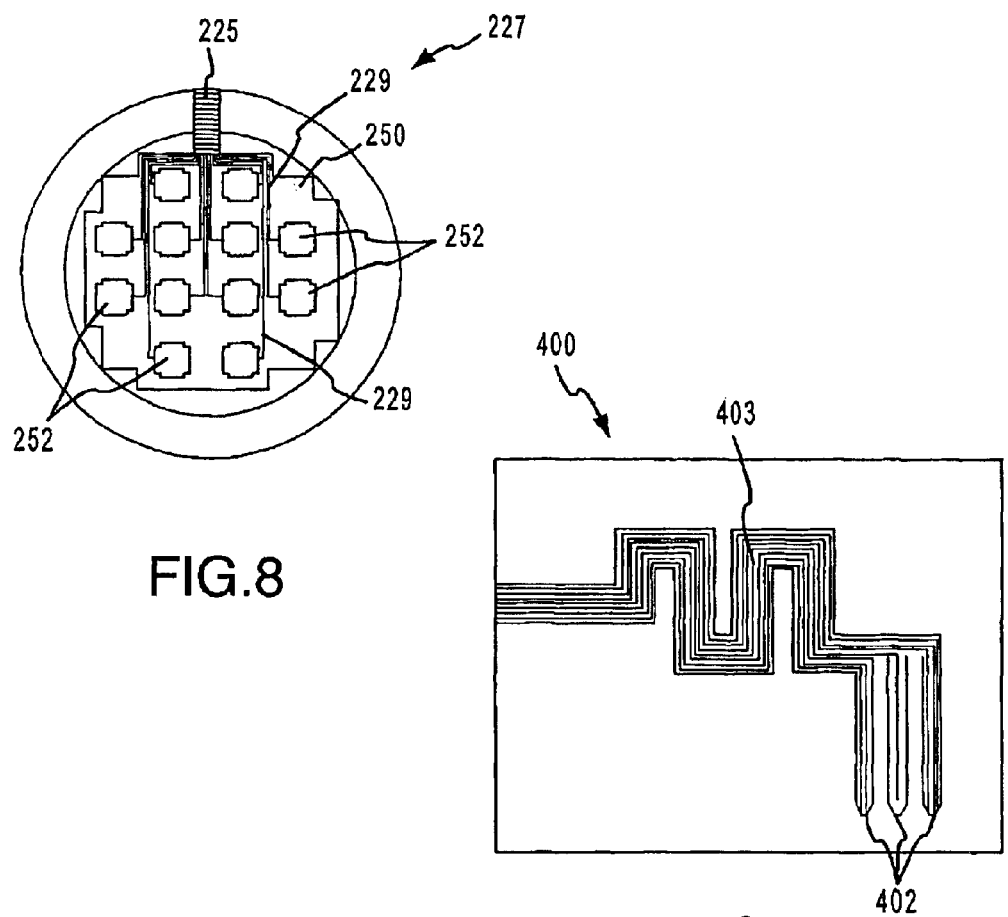
FIG.8
FIG.9

DEVICE FOR CREATING A NEURAL INTERFACE AND METHOD FOR MAKING SAME

This application claims the benefit of Provisional Application No. 60/193,031, filed Mar. 29, 2000.

Financial assistance for this project was provided by the U.S. Government under the following grant numbers: NIH Grant No. S-R29-DC03070-04, N-01-NS62347 and NSF Grant No. BES9624636. The United States Government may own certain rights to this invention.

FIELD OF THE INVENTION

The present invention relates, generally, to a device for creating a neural interface with the central nervous system and a method for making the same. More particularly, the present invention is directed to a device for creating a multi-channel neural interface for long-term recording or stimulation in the cerebral cortex.

BACKGROUND OF THE INVENTION

Since the advent of the simple intracortical single microelectrode four decades ago, continued technical advances in the biological, materials and electronics fields have fueled a steady advance in the development of neural interfaces. Today, advanced devices that are available for implantation into the brain have multiple electrode sites, are chronically implantable, and can include circuitry for on-board signal processing. These complex structures are ideal for many potential clinical applications and basic research applications. For example, there is continuing evidence that a neural interface providing reliable and stable long-term implant function could be used for the realization of clinically useful cortical prostheses for the blind. In addition, the utility of multi-electrode arrays has already been demonstrated in basic research studies which have provided fundamental insights into parallel processing strategies during sensory coding in the brain. However, the complex neural interfaces available today have not yet demonstrated the necessary longevity required to support greater strides in the basic neurophysiological research or clinical neuroprosthetic fields. These gains will only be possible when electrode systems can be made to function reliably and consistently for the lifetime of the implanted subject.

Development of the first single penetrating electrode device spawned the first of three generations of intracortical neural interfaces. In the first generation, microelectrodes consisted of known electrically conductive materials that were stiff enough to be inserted through either the pia or the dura membrane without buckling. These microelectrodes are still in use today and may consist of simple materials such as a stiff and sharpened insulated metallic wire or a drawn glass pipette filled with an aqueous conductor. Because of their high impedance and small site sizes, these electrodes must be rigorously positioned near their target neurons using precision micromanipulation in order to be effective. Recordings can only be held for several minutes to several hours with these microelectrodes before repositioning is required which reduces their attractiveness for long term chronic implant.

The first generation devices have been upgraded and researchers now routinely employ multiple single microelectrodes aligned into arrays to provide ever-increasing numbers of electrode sites in one device. Some devices have positional electrodes while others have modified single electrodes (with larger site sizes and/or reduced impedances) which are capable of recording neural activity without precise positioning. These devices can remain functional upon implant for one to twelve months but the same individual neurons can not be 'tracked' for longer than about six weeks.

The second generation of implantable neural interfaces includes complex electrode designs which allow for batch fabrication of multiple-site devices. These devices are usually monolithic, multi-site devices having the capability for integrated electronics and cabling, and are created by incorporating planar photolithographic and/or silicon micromachining manufacturing techniques from the electronics industry. Devices made of silicon, or devices incorporating molybdenum, that are stiff enough to penetrate the pia upon implantation have been used for recording or stimulation of the cerebral cortex. Like first generation devices, these intracortical interfaces can remain secure in the brain for extended periods of time but recording quality and electrode yield typically diminish with time. Other devices are polyimide-based and have been designed to provide a conformal coverage when placed upon the curved surface of the brain but many of these applications require electrodes to be implanted into the cortex.

A third generation of implantable neural interfaces has developed in the last decade. These latest intracortical electrodes incorporate 'bioactive' components and use standard electrically conductive materials in combination with biologically active species in an effort to improve the performance and function of the neural interface. For example, by 'seeding' a non-traditional glass microelectrode with the active biospecies nerve growth factor (NGF), Kennedy et al. have succeeded in creating a neural interface which actively promotes neurite growth towards the recording site. *J Neurosci. Methods*, vol. 29, no. 3, pp. 181–193 (September 1989). These so-called 'cone electrodes' are only single channel devices but their efficacy is remarkable. The signal to noise ratio of the recorded signals are five to ten times those found in second generation devices and the signals remain stable over extended implant durations. Nevertheless, these third generation devices, like the first and second generation devices, have failed to function reliably and consistently for the lifetime of a subject having the device implanted.

The promise of advanced neuroprosthetic systems to significantly improve the quality of life for a segment of the deaf, blind, or paralyzed population hinges on the development of an efficacious and safe neural interface for the central nervous system. Accordingly, there is a need for a reliable, consistent, and long-term neural interface device for the central nervous system which overcomes the shortcomings of the first, second and third generation devices described above.

SUMMARY OF THE INVENTION

Briefly, the present invention is directed to a thin-film polyimide-based, multi-channel intracortical interface for the central nervous system which is manufactured with standard planar photo-lithographic complementary field-effect transistor (CMOS)-compatible techniques. Electrode sites of the present invention device are preferably gold pads with gold traces (leading to a connector) sandwiched in a mechanically 'flexible' and electrically insulating polyimide substrate. The flexibility of the polyimide is intended to provide a strain relief against the forces of 'micromotion' between the tissue and the implanted device and also allows for the device to be manipulated into a three-dimensional structure. In addition, the polyimide surface chemistry is amenable to modifications and preparations which allow a host of bioactive organic species to be either adsorbed or covalently bonded to its surface. Device flexibility and bioactivity are intended to provide an optimal implant environment and extend the longevity of the tissue-electrode interface. The device structure may also have an integrated polyimide cable which provides for efficient contact points for a high-density connector.

In accordance with one embodiment of the present invention, an implant device for creating a neural interface with the central nervous system includes at least one electrode sandwiched within a bi-layer polyimide insulating substrate and at least one via formed within the bi-layer polyimide substrate. In accordance with a further aspect of the present invention, the electrode and via are located on a shaft of the device and the device can then be connected to a connector by way of an integrated polyimide cable and feedthrough interconnect system. The device preferably includes more than one shaft with each shaft having at least one electrode thereby forming an array of electrodes. Each shaft may also include more than one via in which a bioactive species is placed to help create the ideal device-tissue interface. Separate vias may contain different and distinct bioactive species.

In accordance with another aspect of the invention, the shafts may be bent to form a three dimensional device wherein only the shafts would be implanted into the corticle mantle. This capability provides a mechanism to create a wide range of devices capable of contacting many neurons within a localized volume.

In another embodiment of the present invention, a method for making an implant device for creating a neural interface with the central nervous system is presented which includes the steps of growing an oxide layer on a silicon substrate, depositing and processing a first polyimide layer, depositing and patterning a conductive layer, depositing and processing a second polyimide layer, and dissolving the oxide layer. In other aspects of the method of the present invention, additional process steps may be included such as curing steps to preserve structures and etching steps to prepare a surface for additional processing and/or to clear away unwanted matter. Once electrodes of the device are released by dissolving the oxide layer, the electrodes are securely fitted on connectors which are in turn secured to a subject via use of an adhesive.

BRIEF DESCRIPTION OF THE DRAWINGS

The present invention will hereinafter be described in conjunction with the appended drawing figures, wherein like numerals designate like elements in the various figures, and wherein:

FIG. 7 is a three shaft device in accordance with the present invention with an integrated polyimide cable and a simplified feedthrough interconnect system with the three shafts of the device shown magnified;

FIG. 8 is an interconnect system shown in place on the backside of a twelve pin connector;

FIG. 9 is a six site, three shaft device in accordance with the present invention shown with an 'S' curve;

DETAILED DESCRIPTION OF EXEMPLARY EMBODIMENTS OF THE PRESENT INVENTION

The present invention is directed to flexible polyimide-based intracortical electrode arrays with bioactive capability and a method for making the same. The electrodes in the device of the present invention were constructed by surface micromachining photosensitive polyimide and gold/chromium metal layers on top of oxidized silicon wafers.

Figure 1:
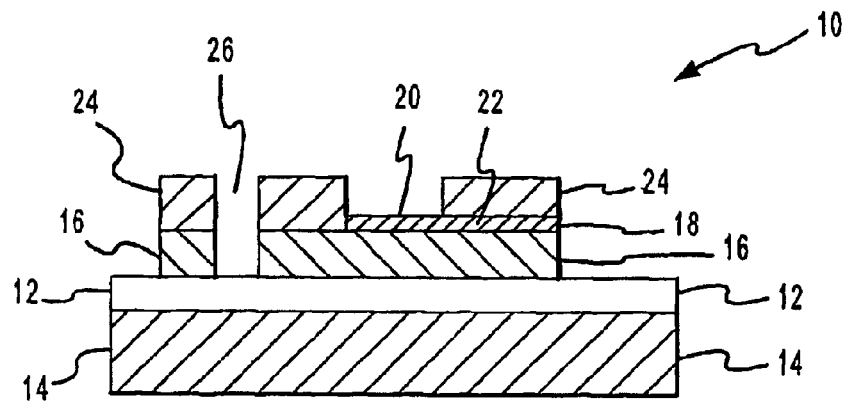
FIG. 1 is a partial cross-sectional view of one embodiment of the device of the present invention.

A partial cross-sectional view of one embodiment of the implant device comprising a polyimide electrode array of the present invention is shown in FIG. 1. The implant device for creating a neural interface with the central nervous system includes at least one electrode sandwiched within a bi-layer polyimide insulating substrate and at least one via formed within the bi-layer polyimide substrate. In order to create the electrodes and via contained in the partial implant device 10 of the present invention, an oxide layer 12 is grown on the surface of a bare silicon wafer 14. A first polyimide layer 16 is deposited over oxide layer 12 and patterned using standard photolithography techniques for subsequent processing. A metal layer 18 is then deposited over first polyimide layer 16 and patterned to form electrode 20 and wire trace 22. A second polyimide layer 24 is then deposited and processed to reveal desired conducting surfaces such as electrode 20. A via 26 is also formed within first and second polyimide layers 16, 24 during processing of the layers to form the implant device 10 of the present invention.

Figure 2:
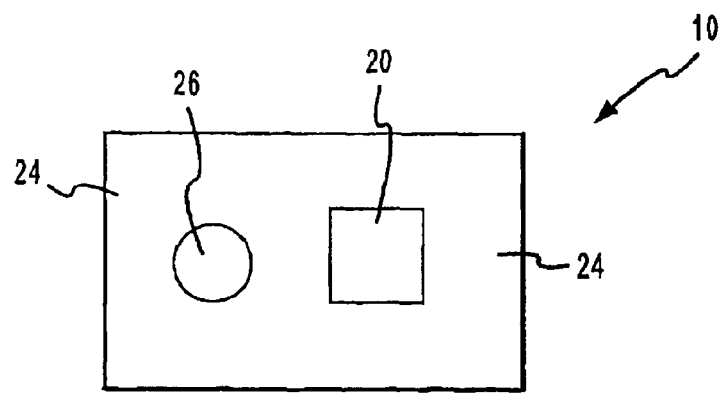
FIG. 2 is a top plan view of the device shown in FIG. 1.

A top view of the partial implant device 10 of FIG. 1 is shown in FIG. 2. Via 26 and electrode 20 can be seen through second polyimide layer 24. As described later with reference to FIGS. 4–7 and 9–11, one or more electrodes and vias are preferably located on shafts of the device.

Figure 3:
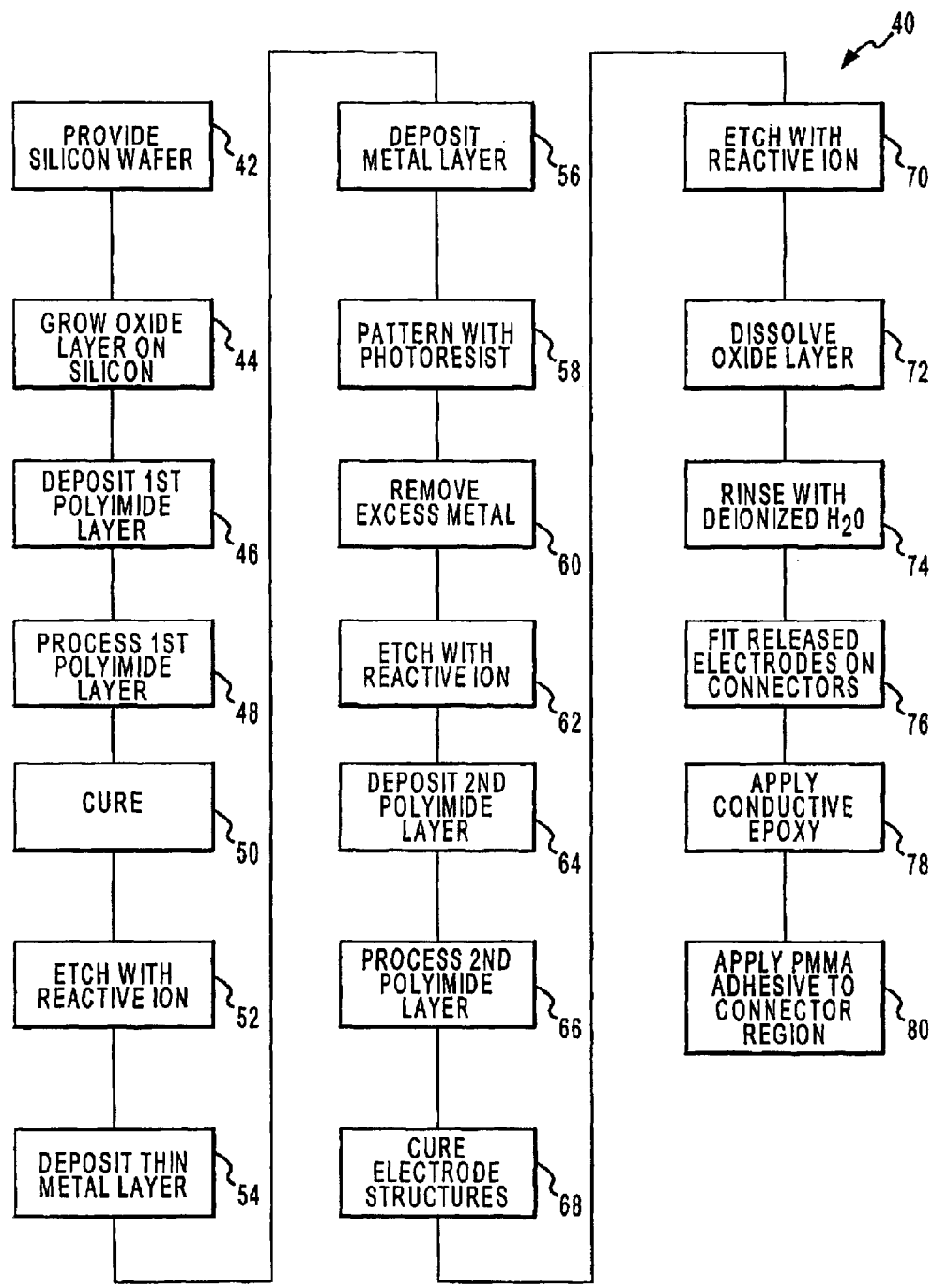
FIG. 3 is a flowchart showing the method of the present invention for making an implant device for creating a neural interface with the central nervous system of an implant subject.

A flowchart showing the method of the present invention for making an implant device for creating a neural interface with the central nervous system of an implant subject is shown in FIG. 3. The method 40 begins by providing a bare silicon wafer in step 42. The silicon wafer is cleaned and etched in an 80 degrees C., 4:1 solution of $H_2SO_4$ and $H_2O_2$. An oxide layer having a thickness of about 0.5 micrometers is then grown on the silicon wafer in step 44 by wet thermal oxidation. A first photo-active polyimide layer is deposited on top of the oxide layer in step 46. The photo-active polyamide is available in a variety of forms from a variety of sources such as Probimide 7520 produced by Arch Chemicals located in Norwalk, Conn. The photo-reactive polyimide may be spin coated onto the oxide layer in step 46 and is preferably deposited until reaching a thickness of about 10–20 micrometers. The first photo-active polyimide layer is then processed by exposing and developing it using standard photolithography techniques in step 48 to define the base of the implant structure of the present invention. The base polyimide layer is then cured in step 50 to protect the developed pattern from subsequent processing steps and to provide a suitable surface for metal deposition. An example of the curing process includes partially curing the base polyimide layer by heating it for about 15 minutes at about 350 degrees C. in a nitrogen purged oven.

The polyimide surface is then etched in step 52 with a reactive ion to micro-roughen the polyimide surface prior to depositing the metal layers. An example of the reactive ion etch includes etching the polyimide surface with $O_2$ at about 50 watts for about 1 minute. A thin metal layer, such as chromium, for example, is deposited onto the etched polyimide surface in step 54. The thin metal layer is preferably about 250 Angstroms thick and may be deposited onto the etched polyimide surface by electron-beam evaporation. The thin metal layer serves as an intermetallic adhesion promoter. Next, a metal layer, such as a layer of gold, platinum, or iridium, for example, is deposited over the thin metal layer in step 56. The metal layer is preferably about 2000 Angstroms thick and may be deposited by evaporating it onto the wafer surface.

A positive photoresist is then patterned over the metal layer in step 58 to delineate the individual recording pads, connecting rings and wire traces of the implant device. Excess metal is then removed in step 60 by etching it away using a gold mask etch, e.g. 10 g. KI, 2.5 g. $I_2$, 100 ml. $H_2O$, for gold and a chrome etch solution, e.g. 1:3 (50 g. NaOH+ 100 ml. $H_2O$): (30 g. $K_3Fe_9CN_8$+100 ml. $H_2O$), for chromium. The resulting wafer surface is then etched in step 62 using a reactive ion to clean and micro-roughen the polyamide/metal structures prior to applying a second polyimide layer. An example of the reactive ion etch includes etching the wafer surface with $O_2$ at about 50 watts for about 1 minute. Next, a second photo-active polyimide layer is deposited over the existing wafer surface in step 64 to a thickness is about the same as or equal to the thickness of the first polyimide layer that was deposited in step 46. The second polyimide layer is then processed in step 66 by exposing and developing it to encapsulate or reveal the desired conducting surfaces. The electrode structures, while on the wafer, are then fully cured in step 68 by heating at about 350 degrees C. for about one hour to complete the imidization process thereby leaving the structures in their final state.

Polyimide shrinks vertically by about 40–50% during the curing process, leaving the final polyimide structures to be less than 20 micrometers thick. Another reactive ion etch, e.g. $O_2$ at about 50 watts for about 1 minute, is then performed in step 70 to remove unwanted organic films and contaminants from the electrodes. After etching, the electrode structures are released from the wafer substrate by dissolving the oxide layer in step 72. The oxide layer that was grown in step 44 may be dissolved using a hydrofluoric acid solution. The resulting structure is then rinsed several times in step 74 with deionized water to remove any unwanted etchant products from the released devices.

Next, the released electrodes are fitted onto connectors in step 76 with the exposed metal contact rings of the interconnect area facing upward as the male connector pins are pushed downwards through the contact rings. Examples of connectors which may be used include a 12-pin connector produced by Microtech, Inc. in Boothwyn, Pa. as part # FR-12S-4 and an 18-pin connector produced by Omnetics, Inc. in Minneapolis, Minn. as Nano series, part # A7855. A small amount of conductive epoxy such as, for example, that produced by Chemtronics of Kennesaw, Ga. as part # AB-5000, is applied in step 78 between each connector pin and its associated ring to complete the electrical connection. Finally, in step 80, a layer of polymethylmethacrylate (PMMA) dental adhesive is applied to the connector region for insulation. This same material is also used to later bond the electrode to the skull. The feed-through interconnect system significantly reduces the labor required to bond the structure to a connector for chronic implantation.

Figure 4:
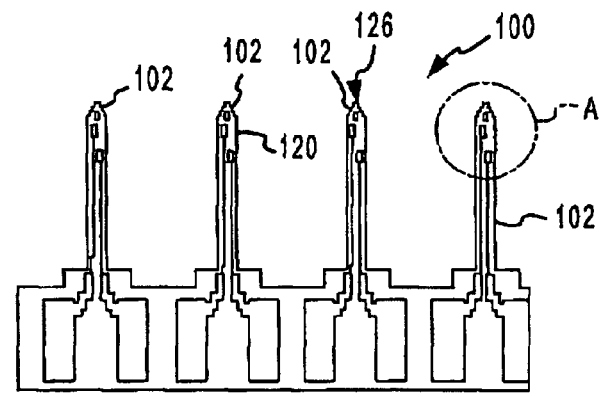
FIG. 4 is a top plan view of a four shaft device in accordance with the present invention.
Figure 5:
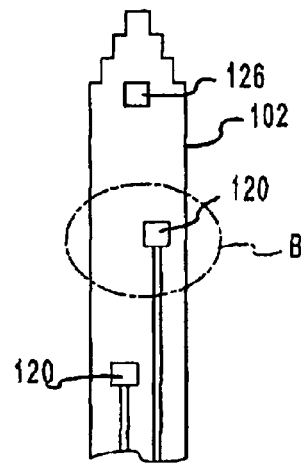
FIG. 5 is a magnified view of area A shown in FIG. 4.
Figure 6:
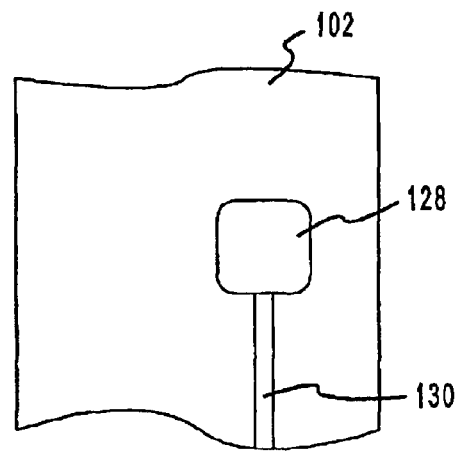
FIG. 6 is a magnified view of area B shown in FIG. 5.

Various embodiments of the chronically implantable polyimide-based 'flexible' intracortical electrode array of the present invention are shown in FIGS. 4–11. FIG. 4 shows a top plan view of a four shaft device 100 in accordance with the present is invention. Device 100 includes four shafts 102 having two electrode sites 120 and a single via 126 at the tip of shaft 102 (See FIG. 5). FIG. 6 shows a magnified view of area B in FIG. 5 which illustrates the exposed gold metal pad 128 which functions as an electrode and the insulated gold wire trace 130 which enables electrical connection to another conducting element.

FIG. 7 shows a three shaft device 200 in accordance with the present invention with an integrated polyimide cable 225 and a simplified feedthrough interconnect system 227 with the three shafts 202 of the device shown magnified. Two of the shafts 202a have exposed electrode sites and multiple vias 226 while one shaft 202b has only a single large ground plane. FIG. 8 shows the interconnect system in place on the backside of a twelve-pin connector. Interconnect system 227 includes connector 250 and twelve connector pins 252. Integrated polyimide cable 225 leads from device 260 (See FIG. 7) while the single wire traces 229 break out to individual connector pins 252. As previously mentioned above, conductive epoxy is used to provide a consistent electrical connection from device 260 to connector 250. A six-site, three shaft device 400 with an 'S' curve 403 engineered directly into the cable for strain relief is shown in FIG. 9. The shafts 402 would be bent at 90 degrees for implant and the cable would run along the surface of the brain to the mounted connector (not shown).

Figure 10:
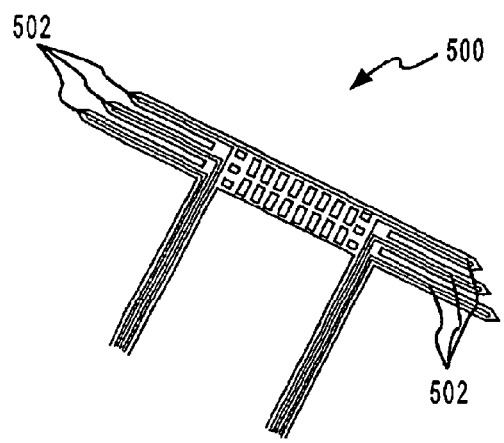
FIG. 10 is a two-dimensional device structure in accordance with the present invention.
Figure 11:
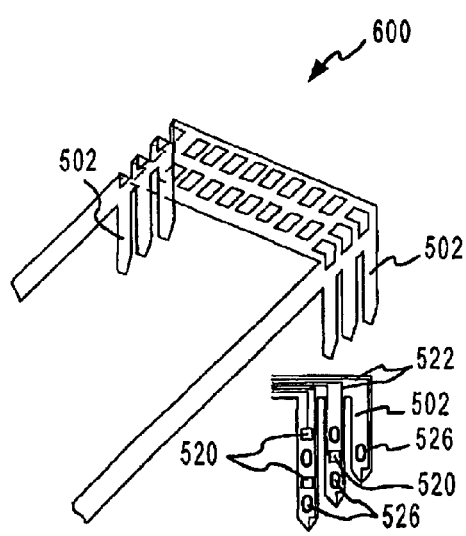
FIG. 11 is the device structure shown in FIG. 10 bent into three-dimensional configuration.

FIG. 10 is a two-dimensional device structure in accordance with another embodiment of the present invention and FIG. 11 is the device structure shown in FIG. 10 bent into a three-dimensional configuration. Two-dimensional device 500 includes shafts 502 having electrodes 520 connected to wire traces 522 and vias 526 (See magnified section of FIG. 11). The shafts 502 of two-dimensional device 500 in FIG. 10 are bent to form three-dimensional device 600 shown in FIG. 11. Only shafts 502 would be implanted into the cortical mantle. As previously stated, this capability provides a mechanism to create a wide range of devices capable of contacting many neurons within a localized volume.

Figure 12:
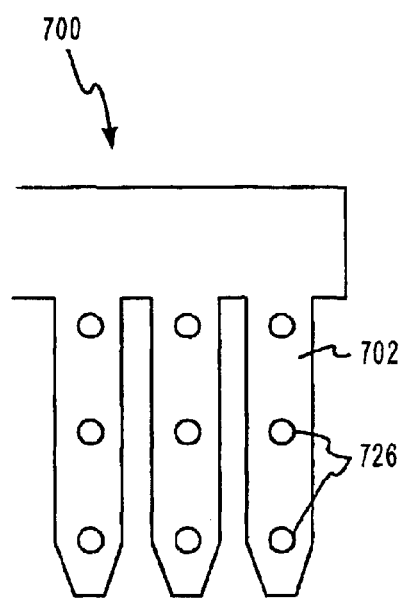
FIG. 12 is another embodiment of the device of the present invention having multiple wells in its shafts.

FIG. 12 is another embodiment of the device 700 of the present invention having multiple wells or vias 726 in its shafts 702. The wells or vias 726 can be selectively filled with the most appropriate bioactive compounds that would help to create the ideal device-tissue interface. For example, one well might contain NGF to attract neuron growth towards an electron site and another well might be filled with Laminin in an effort to create one shaft that acts like an anchor in that Laminin might attract stabilizing extracellular matrix growth. By filling a variety of wells with a variety of bioactive components, intracortical polyimide devices can be engineered for maximum biological acceptance. A micropipette system is used to fill the wells.

Devices intended for successful long-term implant in the nervous system must meet a strict series of criteria in the electrical, mechanical and biological arenas. Electrically, devices must maintain their appropriate insulating and conductive properties over extended implant durations in a saline environment. Mechanically, devices must be capable of withstanding any possible micromotion between tissue and device following implant. Biologically, as a minimal requirement, the device must maintain a biocompatible profile which does not induce and excessive foreign body or immune response. These characteristics were tested on various embodiments of the implant device of the present invention which includes a polyimide electrode array.

Electrical Characteristics of the Present Invention

Basic polyimide electrode-cable assemblies were tested in saline before implantation. Impedance measurements were made using a model 4284A Precision LCR meter (Hewlett Packard Co., Palo Alto, Calif., U.S.A.) which allows for the assessment of complex impedance (resistance, reactance and capacitance) over a large testing frequency range (from 1 Hz to 2 MHz). Saline tests were performed by immersing the shafts and connecting cable of the devices into a 0.9% saline solution at room temperature in a holding chamber sealed from room air. For a single site from each of four devices tested, average initial complex impedance at the standard frequency of 1 kHz was 1837+/−197.3 kOhms (one standard deviation). This value decreased to an average of 355.75+/−307.5 kOhms following two days of soaking, where it remained generally stable over several weeks.

Figure 13:
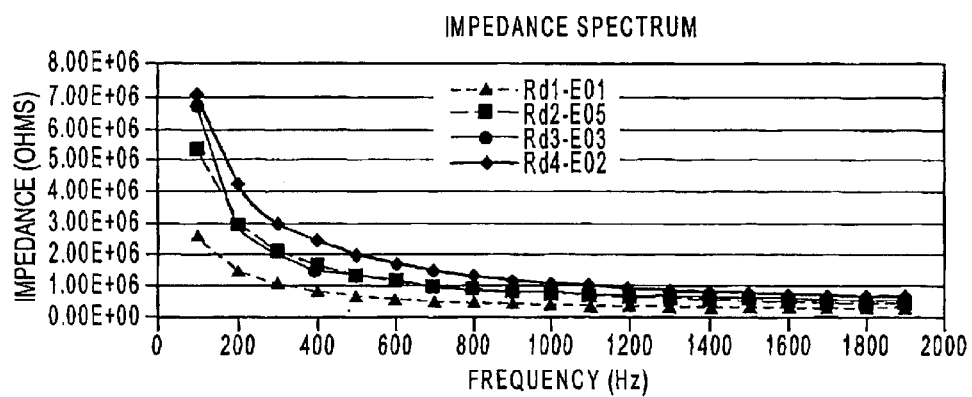
FIG. 13 is a graph showing the impedance spectrum of four devices of the present invention after implant in rats.

Four other devices were implanted chronically into four separate rate somatosensory cortices and impedance values tested 24 hours post-implant. These particular structures had 3, 1.5 mm length shafts per device, with 3 sites (30×30 microns each) per shaft on two shafts (the third shaft had a 1000×50 micron site used for extended ground plane). Testing at the standard 1 kHz frequency revealed the average electrode site impedance (6 sites per device, 24 sites total) to be 190.3+/−25.8 kOhms. FIG. 13 displays the averaged (6 sites per measurement point) complex impedance curves for each implanted device recorded two hours post-implant.

Mechanical Characteristics of the Present Invention

The mechanical characteristics of the intracortical polyimide electrode arrays were investigated using three mechanical tests, indentation, buckling and extended flexing. Indentation test data were used to calculate the estimated Modulus of Elasticity of the polyimide arrays. Buckling and flexing tests were used to probe the mechanical viability of the structures through a 'before and after' impedance measurement. Devices unaffected by mechanical manipulations should exhibit the same impedance before and after the mechanical disturbance.

1) Indentation

Indentation testing was used to calculate an effective modulus of elasticity for the polyimide devices. Measurements were performed on a nanoindentor [an Atomic Force Microscope (AFM) with a nano-indentation tip (no. 10, diamond, Hysitron, Minneapolis, Minn.)]. The sample to be tested was fastened to a mounting disk (15 mm in diameter and 5 mm thick) with epoxy bond glue. The sample and disk were then mounted onto the AFM base. The tip was lowered until contact with the sample was made. The load on the tip and hence the sample was determined. The load was cycled linearly from zero to 250 to zero uN over five seconds. Contact depth, maximum load, slope, contact area, maximum depth, effective depth, the reduced modulus of elasticity and the hardness were logged directly or computed. Testing was completed at 8 random points on a single device. A calculated modulus of elasticity of 2.793 Gpa was obtained.

2) Buckling

Buckling tests were performed using a microdrive (movement resolution of 10.0 E-6 m/step) to hold a single-shaft structure. The structure was lowered perpendicular to a model AE 160 force scale (Mettler-Toledo Inc., Columbus, Ohio) until contact was achieved. Initial buckling forces were determined from the scale reading taken when visual observation confirmed that the structure had buckled. Measurements were repeated 5 times for five different single shaft structures. The mean value of buckling force was calculated to be 0.3694+/−0.0628 g. Theoretical buckling force for a polyimide structure of this size and length is 0.224 g.

3) Extended Flexing

Devices were continuously and repeatedly flexed using a custom made apparatus to test the ability of the polyimide electrode arrays to withstand varying mechanical traumas. Single shaft devices were positioned within the path of a one inch diameter plastic microgear wheel (tooth separation of 1.5 mm) in room air. A 40 Hz sinusoidal input to the gear wheel provided a continuously reversing mechanical stimulus. Shaft flexion of about 45 degrees was obtained as each of two neighboring gear teeth pressed against the flexible shaft in succession. Impedance measurements in saline were taken from 18 electrode sites on 3 different devices before and after at least one million of these mechanical disruptions in each direction. Average percent change in impedance after mechanical manipulations were −8.37%, +2.43% and +9.31% per device (6 sites per device). These results suggest that extended flexing does not induce mechanical breakdown of the conductive traces or electrode sites. Likewise, anecdotal evidence suggests that impedance does not change even after permanent 90% bends are placed into the structures.

Biological Characteristics of the Present Invention

A major promise of polyimide as the insulating substrate for a neural implant is the amenability of its surface chemistry to the attachment of biological species. Bioactive components can be incorporated onto the polyimide surface through simple adhesion or through covalent bonding. By selectively applying various bioactive species to different segments of polyimide devices, structures can be engineered for maximum in vivo performance. The bioactive compounds can be delivered via a variety of carriers. For example, a high concentration of NGF in a fibrin gel may be seeded in a well or via contained within a shaft of the device of the present invention. Seeding is accomplished by micro-injection of the gel into each individual well. The process uses a micropipette that has been pulled to approximately a 10 micron outer diameter (custom-sized to the well dimensions), so that the end of the pipette fits inside the well. The pipette position is controlled with a microinjection system (Patchman and Transinjector 5246, Eppendorf-Netheler-Hinz GmbH, Hamburg, Germany) under a microscope. Starting at one end, the pipette is drawn along the inside surface of the well, allowing capillary action to fill the well. After the well is completely filled, the pipette is repositioned in the center of the well and slowly advanced out of the well, applying a slight suction on the pipette to prevent surface tension from pulling more gel out of the pipette and onto the outside polyimide surface. Other devices have been non-selectively coated with using a resorbable dextran gel, a technique which would allow for the rapid introduction of bioactive material to the local tissue-electrode interface.

Animal Experimentation Using the Present Invention

The device of the present invention has been shown to be capable of chronically recording multi-unit neural activity with reasonable signal-to-noise ratios in the rat barrel cortex.

Rats were anaesthetized with a ketamine-xylazine-aceprozamine mix. Heart rate and oxygen saturation were monitored throughout the sterile procedure. A 4×4 mm craniotomy was performed to expose S1, the rat somatosensory cortex containing the whisker representation (barrel cortex). Traditionally, stiff electrodes for cortical implant are lowered to the surface and entered into the cortical mantle through the dura and pia, or the dura is removed and the electrodes lowered through the pia alone. The low buckling force of the polyimide electrode array precludes the use of this implant tactic. The electrode shafts will always buckle during the insertion attempt before enough force can be generated to create an incision in the pia. Therefore, an alternate technique has been developed and tested to allow for the safe implantation of the flexible device of the present invention. Three pial incisions were created (one for each shaft), either with a #11 scalpel, or a relatively 'stiff' 100 micrometer tungsten wire. The incisions were created to match the shaft spacing pattern. To encourage post-implant recovery, great care was made to ensure that the incisions were made with as little associated tissue damage as possible.

Once the incisions were created, the polyimide devices could be inserted. Chronic cable and connector assemblies were first appropriately positioned by permanently mounting the connector 'can' onto a nearby section of exposed skull with a small amount of PMMA. The polyimide cable leading from the shafts to the connector was about 1 cm. Before final cementing of the can, the electrode shafts were arranged so that they rested naturally near the incisions, preferably with an implied 'bowing' of the integrated cable to provide additional strain relief to the implanted shafts. The electrode shafts were then inserted en masse, by hand, using a #5 forceps viewed with an operating microscope. The device slipped very easily into the cortical mantle through the pia incisions when appropriately aligned. More complex designs incorporating more shafts may require alternate methods for holding and lowering the device. After implant, the protruding cable and any exposed pia were packed with small pieces (1×1 mm) of GELFOAM produced by Pharmacia and Upjohn located in PeaPack, N.J. A final layer of PMMA was applied over the GELFOAM mound thereby sealing the craniotomy. Two external grounds were provided by stainless steel wires attached to an implanted stainless steel bone screw (size 00–80).

Figure 14:
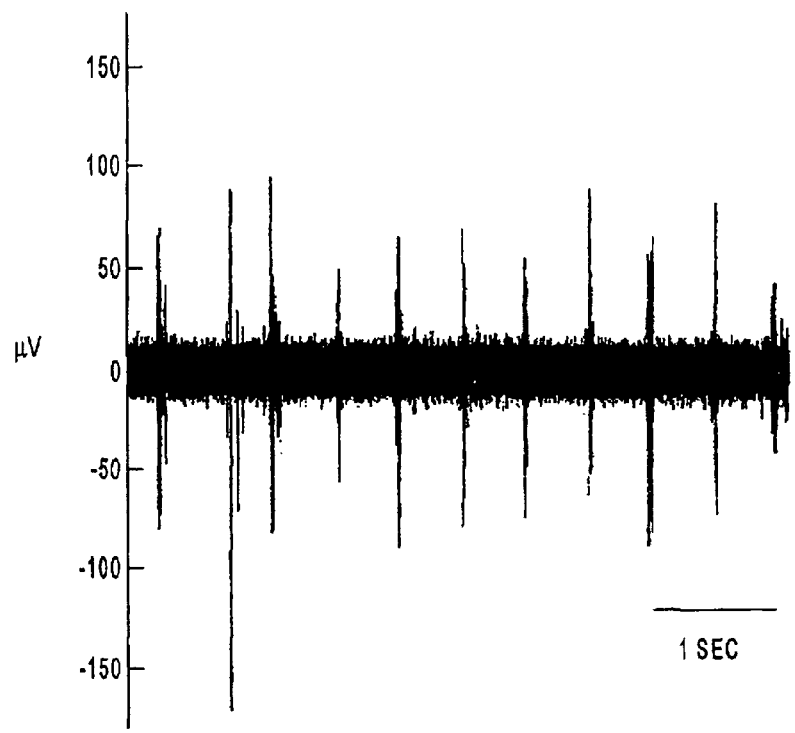
FIG. 14 is a record showing multi-unit neural activity induced by manual contralateral rat whisker stimulation over a six second period.

Recordings were performed in still anaesthetized and in fully awake animals using a MNAP system manufactured by Plexon, Inc, of Dallas, Tex. Signals were buffered with a headstage unity-gain FET amplifier system, then amplified from 20,000–30,000 times and filtered from 300–500 Hz. Multi-unit neural activity indicative of barrel cortex under anesthesia and in the awake state was recorded. Multi-unit firing induced by manual contralateral whisker stimulation over a six second period is shown in FIG. 14. The stimuli is a repeated manual stimulation of the full whisker set using the wooden shaft of a cotton-tipped applicator. Maximum signal amplitude resulting from this stimulus is about 150 uVolts peak to peak and the maximum SNR is roughly 5:1.

As previously described, the implant device of the present invention is capable of sensing multi-unit neural activity from the cerebral cortex and includes gold electrodes sandwiched in a flexible bi-layer polyimide insulating substrate. Polyimide was specifically chosen in forming the device of the present invention due to three main advantages which enable the device to meet specific design specifications which allow for consistent and long-term recording or stimulation in the cerebral cortex.

The first main advantage of using polyimide in the device of the present invention is its inherent flexibility. Traditionally, electrodes have been constructed using materials known to have excellent electrical properties, with little regard to their mechanical properties. Metal, glass or silicon electrodes all can capably function as neural interfaces. However, these materials are generally stiff and stiff materials create a mechanical impedance mismatch when interfaced with the relatively viscous environment of the neural tissue.

In planar form, the flexibility of the polyimide device is evident in motions orthogonal to the plane of the structure. A device that moves with the brain tissue would be much less susceptible to the problem of micromotion, a problem that confounds stiff implants. The flexibility of the polyimide array in the device of the present invention will provide a significant defense against micromotion. The results of the extended flexing experiments verify that polyimide is capable of long-term mechanical variations without any degradation in electrical performance of the electrode sites or cables. The flexibility tests stressed the polyimide structures more than a million times in opposite directions much further than is likely to occur in situ. Flexibility is also a key feature that is employed in the manufacture of complex three-dimensional devices in accordance with the present invention. The three-dimensional structures require precise 90 degree bends of an originally planar substrate. When performed carefully, these bends do not cause structural damage or interfere with electrical conduction.

Another unique feature of polyimide is its ability to be easily mechanically reworked using a variety of photolithographic techniques or an excimer laser. Small controlled microlesions of the polyimide surface can be formed using these processes. The creation of local pits or grooves can be used to provide a device with a jagged surface profile more amenable to the biological environment. Similar modification of silicon structures have been shown to significantly decrease protein adsorption over smooth, unworked structures upon implant into biological tissue. In addition, the excimer laser can be used to completely ablate small areas of polyimide within the structures. Dispersed throughout the polyimide structure, but avoiding the electrode sites and traces towards the connector, these via holes would provide a more minimal interruption of the cortical mantle and possibly encourage rapid astrocyte regrowth through the implanted structure which might better stabilize the implanted device.

The second major advantage of choosing polyimide as the device substrate is the ability to attach important biological entities to the surface. The previously described Kennedy et al. device demonstrated that a single electrode in the brain seeded with NGF can remain patent and provide usable neural signals. By placing and seeding wells or vias near each recording site, the device of the present invention encourages neurite growth toward each active electrode. Like the previously referenced cone electrode, such growth should boost the signal to noise ration and provide a more stable interface. The polyamide array in the device of the present invention would provide a far larger number of active electrode sites than the single electrode Kennedy device. Also, as previously discussed, attached biomolecules would not need to be limited to NGF. Any appropriate species which could successfully influence the integrity of the tissue-electrode interface can be considered for use in the device of the present invention.

The third major advantage of polyimide is that it can be processed using standard planar photolithographic techniques on silicon wafers which enables rapid prototyping. Electrode design, manufacture and testing can be a lengthy, laborious and expensive operation. The device of the present invention and the method for making it allows for quick turn around on new designs. Full production of each device set takes roughly two to three days depending upon the pattern complexity of the given design. This short time period allows for the efficient assessment of many design parameters such as device shape, thickness, width, and electrode site size, for example. Rapid prototyping also ensures that devices can be custom-tailored to their individual implant requirements. Such factors as implant shape and depth will vary from animal to animal or in various clinical subjects Therefore, rapid prototyping is beneficial both in the development stage and in the production of various differing structures.

It should be understood that the foregoing description is of exemplary embodiments of the invention and that the invention is not limited to the specific forms or structures shown or described herein. Various modifications may be made in the design, arrangement, and type of elements and structures disclosed herein, as well as the steps of making and using the invention without departing from the scope of the invention as expressed in the appending claims.

We claim:

1. An implant device for creating a neural interface with the central nervous system comprising at least one electrode sandwiched within a bi-layer polyimide insulating substrate and at least one via formed within said bi-layer polyimide substrate, wherein said via is separate and apart from said electrode.

2. The device of claim 1 further comprising at least one bioactive species contained within said via.

3. The device of claim 1 further comprising at least one shaft and wherein said electrode and via are located on said shaft.

4. The device of claim 3 wherein said shaft is bent to create a three-dimensional device structure.

5. The device of claim 1 further comprising a feedthrough interconnect system for connecting the device to at least one connector pin.

6. The device of claim 1 wherein said bi-layer polyimide substrate is flexible.

7. An implant device for creating a neural interface with the central nervous system comprising:
   a first flexible thermoplastic layer;
   a second flexible thermoplastic layer;
   a metal layer sandwiched between said first and second layers;
   at least one electrode formed from said metal layer; and
   at least one via formed within said first and second layers, wherein said via is separate and apart from said electrode.

8. The implant of claim 7 wherein said first and second flexible thermoplastic layers comprise a polyimide.

9. The implant of claim 7 further comprising at least one bioactive species contained within said via.

10. The implant of claim 9 wherein said implant comprises at least two or more vias and each of said vias contains a different bioactive species.

11. The implant of claim 7 further comprising at least one wire trace connected to said electrode.

12. The implant of claim 7 wherein said implant is bent to create a three-dimensional structure.

13. The implant of claim 7 wherein said electrode and said via are located on a shaft.

14. The implant of claim 13 wherein said electrode has an exposed site size within a range of about 20–40 microns by 20–40 microns.

15. The implant of claim 13 wherein said shaft is preferably about 1.5 millimeters in length.

16. The implant of claim 13 wherein said shaft preferably has a width of about 160 microns and a thickness of less than 20 microns.

17. The implant of claim 13 wherein said shaft is bent to create a three-dimensional implant.

18. The implant of claim 7 further comprising two or more shafts wherein at least one electrode and at least one via is located on each shaft.

19. The implant of claim 18 wherein said shafts are bent to create a three-dimensional implant.

20. The implant of claim 7 wherein said via is preferably located about 40 micrometers from said electrode.

21. The implant of claim 7 further comprising a feedthrough interconnect system for connecting the implant to at least one individual connector pin.

22. An electrode array for creating a multi-channel neural interface with the central nervous system comprising:
   at least two electrodes sandwiched within a bi-layer polyimide insulating substrate; and
   at least one via formed within said bi-layer polyimide insulating substrate wherein said via is separate and apart from said electrodes.

23. A The electrode array of claim 22 further comprising at least one bioactive species contained within said via.

24. The electrode array of claim 22 further comprising at least one shaft wherein said electrodes and said via are located on said shaft.

25. The electrode array of claim 24 wherein said shaft is bent to form a three-dimensional structure.

26. The electrode array of claim 24 further comprising a plurality of electrode recording pads connected to said electrodes via a feedthrough interconnect system.

27. The electrode array of claim 26 further comprising a separate connector pin connected to each of said recording pads.

28. A method for making a device for creating a neural interface with the central nervous system comprising the steps of
   providing a silicon substrate;
   growing an oxide layer over said silicon substrate;
   depositing and processing a first polyimide layer over said oxide layer;
   depositing and patterning a conductive layer over said first polyimide layer;
   depositing and processing a second polyimide layer over said conductive layer to form at least one electrode and at least one via in said polyimide layers wherein said via is separate and apart from said electrode; and
   dissolving said oxide layer.

29. The method of claim 28 wherein said electrode and via are located on a shaft of the device which can be bent to form a three-dimensional configuration.

30. The method of claim 29 wherein an electrode array and multiple vias are formed within one or more shafts to provide a multi-channel neural interface.

31. The method of claim 28 further comprising the step of curing a surface of the device after the steps of depositing and processing the first and second polyimide layers.

32. The method of claim 31 further comprising the step of etching a surface of the device with a reactive ion after curing roughen the surface of the device for further, processing.

33. The method of claim 28 further comprising the step of fitting the electrode released from the dissolving step on at least one connector.

34. The method of claim 33 further comprising the step of applying a conductive epoxy to a connector site to complete an electrical connection between the electrode and connector.

35. The method of claim 34 further comprising the step of applying an adhesive to the connector site for adhering the device to a subject.

* * * * *